United States Patent [19]

Williamson et al.

[11] Patent Number: 4,883,462
[45] Date of Patent: Nov. 28, 1989

[54] BLOOD EXTRACTION ASSIST APPARATUS AND METHOD

[75] Inventors: Warren P. Williamson, Huntingdon Beach; Donald W. Schoendorfer, Santa Ana, both of Calif.

[73] Assignee: Baxter Travenol Laboratories, Inc., Deerfield, Ill.

[21] Appl. No.: 8,753

[22] Filed: Jan. 30, 1987

[51] Int. Cl.$^4$ ............................................ A61M 25/00
[52] U.S. Cl. ...................................... 604/53; 604/66; 128/64
[58] Field of Search .................. 128/327, 60, 1 D, 64; 604/4, 53, 37, 66, 50

[56] References Cited

U.S. PATENT DOCUMENTS

| | | |
|---|---|---|
| Re. 31,668 | 9/1984 | Popovich et al. |
| 3,592,183 | 7/1971 | Watkins et al. |
| 3,699,960 | 10/1972 | Freedman |
| 3,811,800 | 5/1974 | Shill |
| 3,824,992 | 7/1974 | Nicholson et al. |
| 3,878,839 | 4/1975 | Norton et al. |
| 3,892,229 | 7/1975 | Taylor et al. |
| 4,003,371 | 1/1977 | Fischer |
| 4,066,084 | 1/1978 | Tillander |
| 4,086,924 | 5/1978 | Latham, Jr. |
| 4,191,182 | 3/1980 | Popovich et al. |
| 4,205,688 | 6/1980 | Hauser et al. |
| 4,321,929 | 5/1982 | Lemelson et al. |
| 4,350,156 | 9/1982 | Malchesky et al. |
| 4,425,114 | 1/1984 | Schoendorfer et al. |
| 4,479,494 | 10/1984 | McEwen |
| 4,498,983 | 2/1985 | Bilstad et al. |
| 4,548,198 | 10/1985 | Manes |
| 4,648,866 | 3/1987 | Malbrancq et al. |
| 4,667,672 | 5/1987 | Romanowski |
| 4,671,290 | 6/1987 | Miller et al. |
| 4,715,849 | 12/1987 | Gion et al. |

OTHER PUBLICATIONS

Jacobson et al, "Medicine and Clinical Engineering", p. 568.
Kantrowitz, "Introduction of Left Ventricular Assistance", vol. XXXIII, Trans. Am. Soc. Artif. Intern. Organs 1987, pp. 39–48.

*Primary Examiner*—Michael H. Thaler
*Attorney, Agent, or Firm*—Nixon & Vanderhye

[57] ABSTRACT

A limb stimulator is engaged with a lower portion of a patient's limb for facilitating sustained venous blood flow therefrom toward a phlebotomy needle when the stimulator is activated. The stimulator may be an inflatable squeeze bulb adapted to engage a human hand and to be squeezed thereby when inflated. The stimulator may also, or alternatively, include a pressurizable member substantially surrounding a lower portion of the limb and adapted to apply external pressure thereto when periodically pressurized so as to periodically (e.g., in approximate synchronism with natural pulsitile blood movements in the limb) express venous blood upwardly through the limb to the needle. Inflation of the hand-held squeeze bulb serves as a tactile stimulus to the patient to assist in venous blood movements towards the needle by muscle and tendon flexure in the lower part of the limb and may also be periodically activated (e.g., in approximate synchronism with natural pulsatile blood movements in the limb).

17 Claims, 4 Drawing Sheets

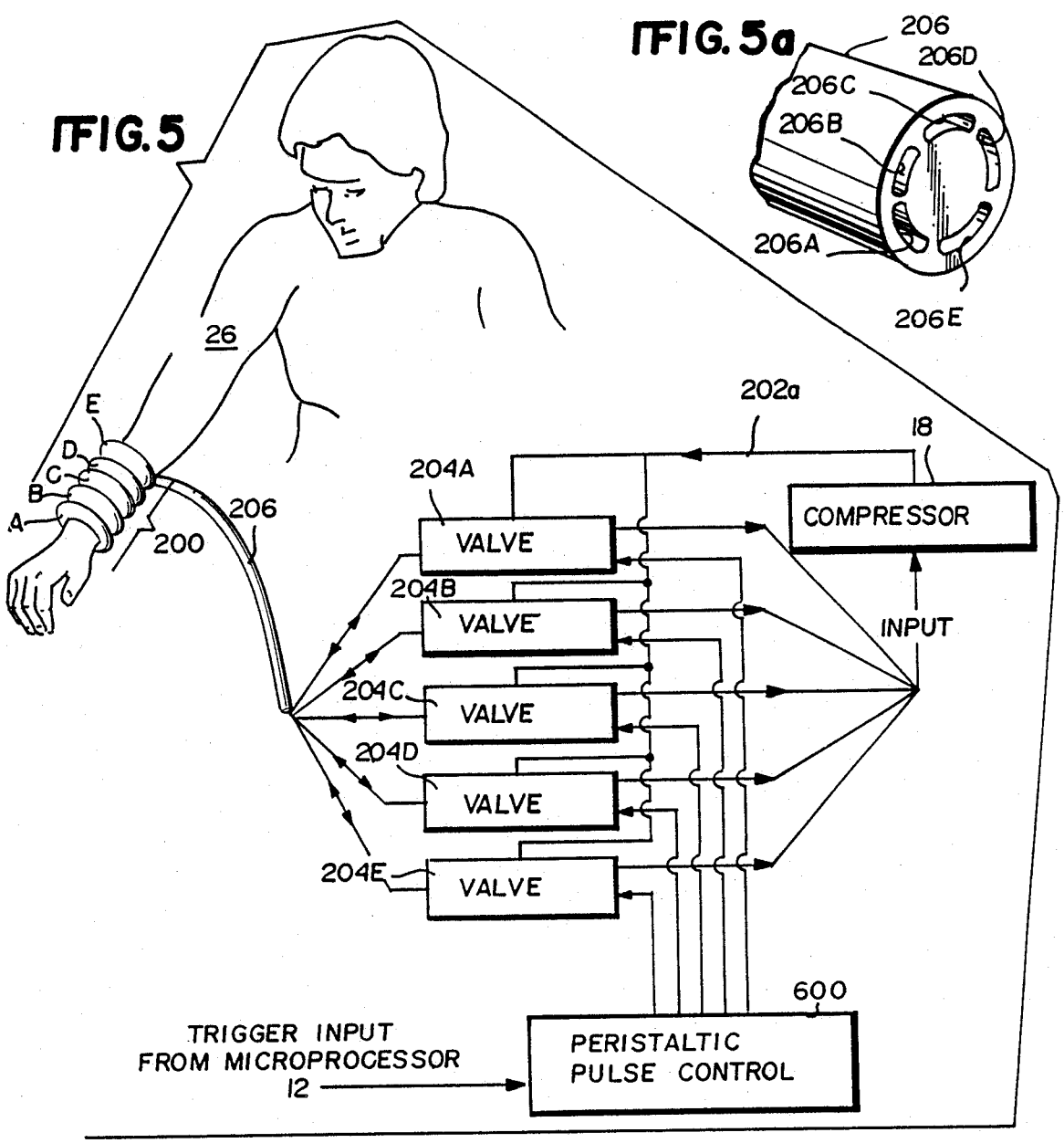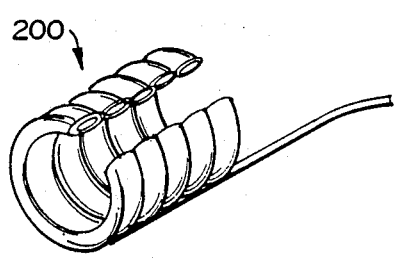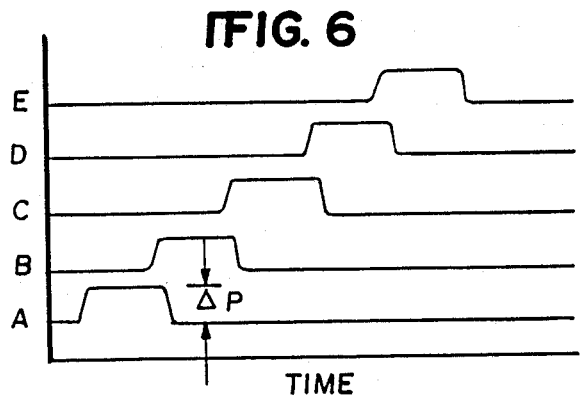

BLOOD EXTRACTION ASSIST APPARATUS AND METHOD

This invention is generally directed to blood extraction and processing apparatus and method—and to the interaction between a blood donor and a blood extraction machine. It is particularly directed to apparatus and method for selectively facilitating sustained venous blood flow to a blood extraction needle located in the vein of a human upper limb during blood extraction processes.

For many purposes, blood is often extracted from a human patient via a venous phlebotomy needle located near a mid-portion of a human upper limb. The purpose for such blood extraction may be to collect some predetermined quantity of blood or it may involve more elaborate blood processing steps (e.g., plasmapheresis, plateletpheresis, etc.) before the processed blood (or some component thereof) may even be returned to the patient's body via the same needle (or possibly through another needle situated elsewhere in the patient's body).

In any event, it is typically desirable to maximize the rate at which blood is extracted from the patient consistent with patient comfort and a particular patient's physiology. Maximizing the blood extraction rate not only minimizes required patient hook-up time, it also increases the number of patients which can be handled by a given physical system within a given time and thus enhances the economics of the system's operation.

A conventional blood pressure cuff is typically inflated to about 40 mmHg during blood extraction procedures. This conventional blood pressure cuff is located on the limb above the extraction point. It is inflated to a pressure above the expected venous pressure (e.g., 0–10 mmHg) so as to occlude venous blood return flows (thereby pooling venous blood in the lower limb veins) without occluding the relatively higher arterial blood flow pressures (e.g., 60–120 mmHg).

It has long been known that such blood extraction rates can be increased if the patient periodically squeezes his/her hand into a tight fist configuration. Presumably, this is because the associated muscles and tendons in the lower part of the limb are thus caused to exert pressure against the veins in the lower limb and to physically express blood contained in those veins upwardly in the general direction of the blood extraction needle. Then, when the fist is relaxed, additional arterial blood is permitted to flow more freely into the lower portion of the limb to again accumulate a supply within the veins in readiness for the next fist squeezing/blood expression cycle.

Some examples of possibly relevant prior art approaches to blood flow assistance are set forth in:
U.S. Pat. No. 3,592,183—Watkins et al (1971)
U.S. Pat. No. 3,699,960—Freedman (1972)
U.S. Pat. No. 4,425,114—Schoendorfer et al (1984)
U.S. Pat. No. 4,479,494—McEwen (1984)
U.S. Pat. No. 4,498,893—Bilstad et al. (1985)

Watkins et al uses inflatable flow assist devices inserted in the aorta and synchronously pulsed with the patient's pulse to assist blood flow through the heart. Freedman describes a dialysis system which simultaneously extracts and returns blood to two patients using pumps to assist blood flows—but with no apparent attempt to otherwise stimulate blood flows. Schoendorfer et al is perhaps the most pertinent because the blood extraction pump is powered by fist exercise of a flexible pressure bulb—which therefore necessarily also facilitates blood flow within the limb if the patient properly operates the pump. McEwen et al uses automated inflation of a pneumatic tourniquet for restricting blood flow in a limb during surgical procedures. Bilstad et al automatically inflates the usual blood pressure cuff during each blood draw cycle and deflates it during each blood return cycle of a cyclic blood processing system.

A series of sequentially activated inflatable bladders have also been used to externally stimulate venous blood flows in the limbs of patients having poor circulation. Some such prior approaches may be described in publications (identity presently unknown) of the late 1970's.

As will be seen, none of these prior art approaches provides selective automated tactile stimulus or tactile pumping action to the limb so as to facilitate proper blood flow in the limb during blood extraction processes.

In many typical prior art arrangements, the patient may be given a flexible hand grip member of some sort and then signalled (either audibly or visually or both) in an attempt to stimulate the patient to engage in periodic fist squeezing exercises. For example, plasmapheresis and/or plateletpheresis apparatus marketed in the past by HemaScience Laboratories Inc. includes a controlled light indicator intended to provide a visual indication of blood flow and, accordingly, inherently also providing a visual stimulus to the patient when to begin fist squeezing exercises so as to improve an inadequate flow indication.

Unfortunately, many patients fail to consistently follow such audio-visual stimulus signals—sometimes to the extent that occlusions in blood flow occur setting off alarms and requiring the assistance of monitoring technicians before the blood extraction process can be continued. Typically, some patients become confused by visual stimuli (especially when there are an array of visible lights within view) and by audible stimuli (especially when there are many machines in a common environment, some of which may be simultaneously "beeping"). Furthermore, to help pass time, many donors wear head-phones and/or watch television programs, sleep, or the like thus making it difficult to simultaneously concentrate on the superimposed audio/visual stimuli associated with the blood processing system.

To further confuse matters, some sophisticated blood processing systems require an initializing phase during which the patient must not flex muscles in the limb from which blood extraction is to occur. For example, during this initialization period, the blood processing system may be programmed to take various flow/rate/pressure data unique to that patient's physiology so as to construct an optimal flow control algorithm for later use during the actual blood extraction cycle. If the data collected during this initializing procedure does not truly represent steady state conditions with the limb muscles at rest, then a considerably less than optimum control algorithm may be employed during the blood extraction cycle. On the other hand, some other types of existing blood processing systems require the donor to begin pumping the fist immediately upon inflation of the conventional blood pressure cuff located at the upper portion of the donor's limb. Accordingly, if a donor has accumulated experience on this type of system, it is understandably confusing when he/she is then hooked up to a system of another type and requested not to being exercising the fist until a subsequent visual or audio signal is perceived (by which time the donor may be absorbed in a radio or television program, tape recorded audio entertainment, etc.).

We have now discovered a novel blood extraction assist apparatus and method which utilizes a limb stimulator adapted for active engagement with a lower portion of the limb from which blood is being extracted. The stimulator may be designed in one or more different manners so as (a) to merely provide a more positive tactile stimulus for the donor to begin exercising his/her fists or (b) to provide a positive externally applied pumping action of its own. In any event, the stimulator is adapted to physically engage a lower portion of the limb and to facilitate sustained venous blood flow upwardly therein to the blood extraction needle when activated.

In the most simple embodiment, the stimulator may include an inflatable squeeze bulb engaged with the donor's hand so as to provide a significant squeeze resistance thereagainst when inflated. In this embodiment, the bulb remains in a deflated flaccid state (wherein it provides essentially zero squeeze resistance) at any time when fist exercises are not desirable (e.g., during preliminary data taking procedures). However, when the active blood extraction cycle begins, the squeeze bulb is inflated so as to provide tactile stimulus to the donor indicating that it is now time to perform fist exercises. It also directly provides a flexible substance against which the fist conveniently may be flexed or squeezed. If desired, the internal pressure of the squeeze bulb can be pulsed (e.g., perhaps, if desired, in approximate synchronism with the donor's detected pulse or a subharmonic thereof) so as to encourage a "lazy" donor to squeeze faster.

In the exemplary embodiment, only a few changes are required to an existing computer controlled blood processing apparatus to implement the tactile feedback squeeze bulb embodiment. For example, if the blood processing apparatus is already controlled by a microprocessor, suitable changes to the program of that processor may permit it to control an air valve connected to an existing air compressor (e.g., already present and used to inflate a conventional blood pressure cuff located at the upper part of a limb) through which the inflatable squeeze bulb is either pumped up or deflated (e.g., by controlling a three-way valve to exhaust the squeeze bulb to atmospheric pressure or to the compressor input) under microprocessor control so as to give the donor instant feedback when fist squeezing operations are to be conducted.

The squeeze bulb may be connected to the computer controlled three-way valve and pressurized air source with a rubber hose similar to that used for attaching the traditional blood pressure cuff. The squeeze bulb remains very limp when deflated (e.g., when exhausted). However, when the blood collection cycle begins, the pressurized air source is permitted to pump up the squeeze bulb (e.g., via the computer controlled three-way valve) and then hold this pressure by shutting such valve (it may also be caused to pulse so as to encourage a lazy donor to squeeze faster if desired).

Throughout the blood collection process, the donor is expected to continue periodically squeezing the inflated squeeze bulb. Then, when the blood collection process has been completed, the squeeze bulb is deflated under computer control (e.g., by moving the three-way valve so as to exhaust the squeeze bulb to atmospheric pressure or to the compressor input). In this manner, the squeeze-bulb is selectively activated so as to provide positive tactile feedback leaving the donor free to talk or to listen or watch other audio or visual stimuli while still insuring that the donor is positively signalled in an unmistakable way when fist exercises are desired.

While the controllably inflated squeeze bulb provides tactile stimulus and thus improves communication with the donor, it is still possible for unmotivated donors including those who may fall asleep) or confused donors (e.g., those who intuitively feel that they should begin flexing their muscles as soon as they feel the blood pressure cuff inflate) to react improperly.

Accordingly, in yet another embodiment of this invention (which may be used simultaneously with the squeeze bulb or separately), the limb stimulator in engagement with the lower portion of the limb actively and directly exerts external compression (e.g., of the donor's hand and/or part of his lower arm) in a periodic timing sequence (e.g., if desired, in synchronization with the natural pulsatile blood movements of the limb or a submultiple thereof) so as to itself actively express venous blood upwardly through the limb to the needle. This second more active embodiment also may be controlled by the existing microprocessor of existing blood processing apparatus if a program of that processor is suitably changed to control periodic activation of the circulatory assist cuff. This second embodiment thus attempts to avoid virtually all problems of interfacing the donor with a blood extracting machine and any possible confusion of the donor with respect to audio/visual/tactile stimuli. It also tends to optimize blood extraction procedures with a non-motivated donor since the donor needs do nothing except remain connected to the system.

These as well as other advantages and objectives of this invention will be more completely appreciated and understood by carefully reading the following detailed description of presently preferred exemplary embodiments of this invention taken in conjunction with the accompanying drawings, of which:

FIGS. 5, 5a and 5b illustrate yet another alternative embodiment of the circulatory assist cuff utilizing a series of sequentially inflated cuffs; and FIG. 6 illustrates one possible activation sequence for the series of cuffs A-E shown in FIG. 5.

Figure 1:
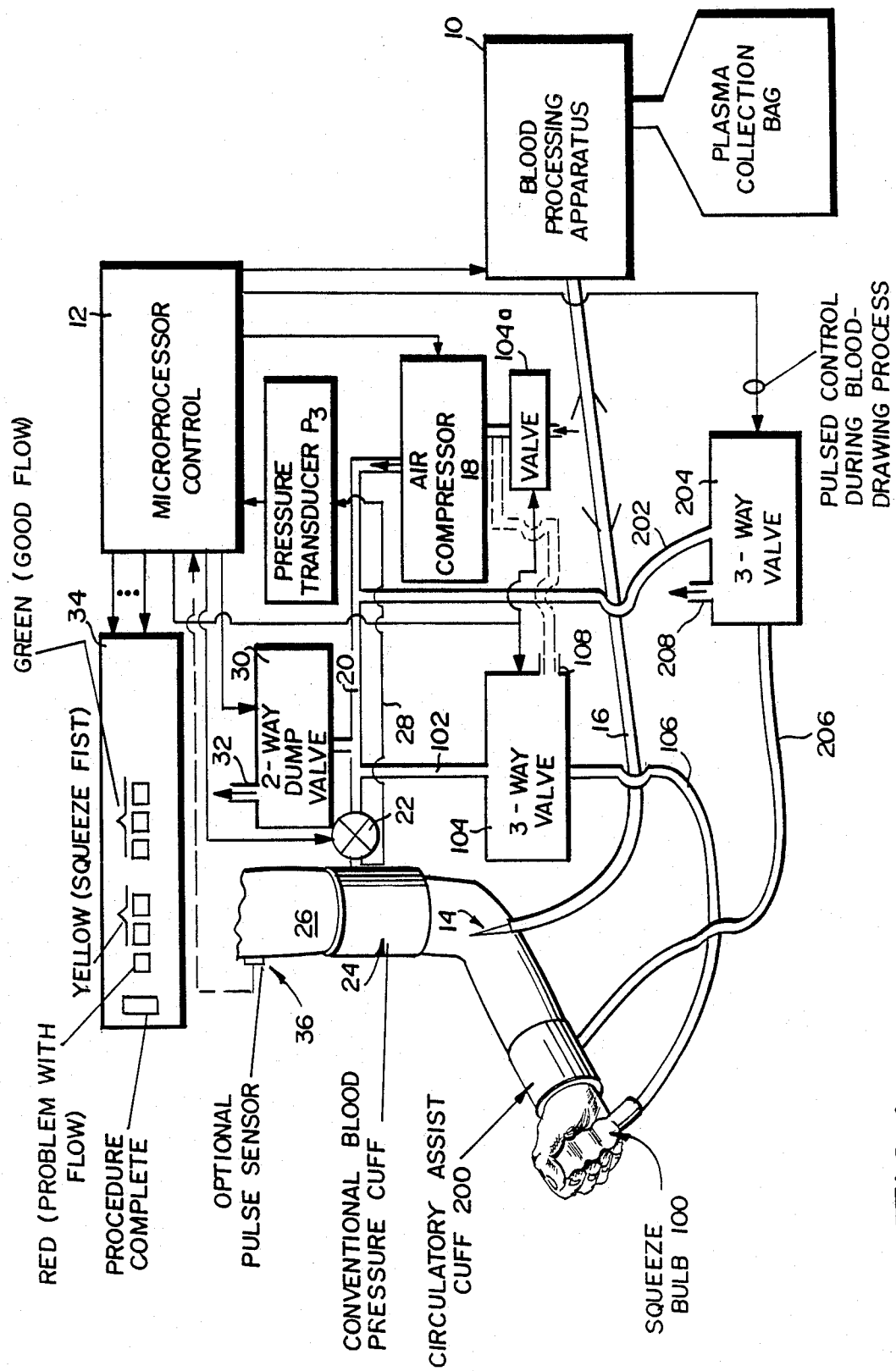
FIG. 1 is a simplified block diagram illustrating both the squeeze bulb embodiment and the exercise cuff embodiment of this invention in the context of a single integrated system (each embodiment can, of course, be employed singly if desired)

FIG. 1 schematically depicts a typical blood processing system modified in accordance with this invention. Blood processing apparatus 10 (e.g, plasmapheresis, plateletpheresis, etc.) is typically under control of microprocessor 12. Blood to be processed is extracted through a phlebotomy needle 14 and associated tubing 16. An air compressor 18 or other source of pressurized gas supplies a pressurized air conduit 20 which, via computer controlled valve 22 may be utilized for pumping up a conventional blood pressure cuff 24 located on the upper arm or limb of the donor 26. The pressure of cuff 24 is typically monitored by pressure transducer P3 (via conduit 28) and a computer controlled dump valve 30 may be provided for controllably exhausting conduit 20 to atmospheric pressure (or to the air compressor input in association with valve 104a slaved to operation of valve 104) via exhaust port 32. In at least some such blood processing systems, the microprocessor control 12 also selectively activates a light blood flow indicator 34 which, inherently, also provides a visual signal when the donor 26 is supposed to perform fist squeezing exercises so as to improve dangerously low blood flow indications. The donor's actual pulse rate can be monitored through periodic pressure changes in cuff 24 as measured by P3. Alternatively, a conventional pulse sensor 36 may be attached to some portion of the donor's body 26 so as to provide microprocessor control 12 with pulsatile information synchronized to the donor's blood flows.

Just described portions 10-36 of the blood processing system in FIG. 1 are typically already present in some existing automated plasmapheresis systems. For example, in one plasmapheresis system marketed in the past by HemaScience Laboratories Inc., microprocessor control 12 automatically inflates the blood pressure cuff 24 during both an initial data monitoring phase and a subsequent main blood extraction phase. During the data monitoring phase, venous blood pressure is monitored through the phlebotomy needle with the pressure cuff 24 inflated to about 40 mmHg. An intake pump of the blood processing apparatus 10 is commanded to pump approximately 50 ml per minute blood flow while another venous blood pressure reading is recorded. The controller 12 then constructs a control curve describing the unique inferred relationship between blood flow and blood pressure for that particular donor. This "customizing" of the blood extraction algorithm is designed to minimize trauma to the donor's vein while yet extracting blood at a maximum possible rate (up to a desired upper limit of about 100 ml per minute as described in commonly assigned copending U.S. patent application Ser. No. 626,034 filed 22 Nov. 1985). During the time that both these pressure readings are taken during the initial data gathering phase, it is very important that the donor not flex his fist or hand or move the hand because such pressure readings provide accurate useable data only if they represent steady state resting conditions and are not influenced by transients related to muscle motions, etc.

Unfortunately, this process is often confusing to the donor because when cuff 24 is felt to inflate, there may be an intuitive cue for the donor to start pumping his/her fist (especially if he/she has experienced other blood processing systems which sometimes require a donor to begin pumping the fist as soon as blood pressure cuff 24 inflates). Light indicators 34 (and/or similarly controlled audio transducers) may be utilized to visually (or audibly) cue the donor as to the proper time for fist squeezing exercises; however, such visual (or audio) stimuli often fail to produce the desired result for reasons already mentioned.

A considerably improved and more positive tactile feedback to the donor 26 is achieved by adding an inflatable/deflatable squeeze bulb 100 shaped and sized so as to engage a human hand and to be squeezed thereby when inflated. Squeeze bulb 100 conveniently may be pressurized by simply tapping into the existing pressurized air conduit 20 via additional conduit 102, three-way valve 104 and conduit 106 as shown in FIG. 1 The three-way valve 104 is controlled by microprocessor 12 (see one exemplary control program shown in FIG. 2) so as to either connect the squeeze bulb 100 with an exhaust port 108 (to atmospheric pressure thus leaving squeeze bulb 100 totally deflated and with essentially zero squeeze resistance) or inflated via pressurized air from conduit 102. Alternatively valve 104 may actively exhaust bulb 100 by connection to the intake side of compressor 18 with a slaved valve 104a thereby accelerating the exhaust of all air from inside bulb 100. Once inflated, the three-way valve 104 may be further controlled so as to trap a quantity of air inflating squeeze bulb 100 thus providing significant squeeze resistance against which the donor may exert force and thus perform the necessary fist squeezing exercises while simultaneously delivering an unmistakable tactile stimulus to the donor to do so. The control circuit 12 may also be adapted to cause repeated and periodic tactile stimulus-/inflation cycles of the squeeze bulb 100 (e.g., if desired, perhaps in synchronization with the donor's own pulsatile blood movement or a submultiple thereof as sensed by sensor 36 or cuff 24/plasma transducer P3) so as to encourage a "lazy" donor to squeeze faster or at the correct times.

Alternatively, or in addition, an active inflatable circulatory assist cuff 200 may be placed around the donor's wrist at the beginning of the whole procedure. Circulatory assist cuff 200 may also be connected to the existing pressurized air conduit 20 via additional tubing 202, three-way valve 204 and tubing 206. Three-way valve 204 also may be controlled by microprocessor 12. However, it now must be pulsed (e.g., in synchronism with the detector donor blood movement within the limb 26) during the blood extraction phase of the process. During the initial data gathering phase, valve 204 is controlled so as to exhaust the circulatory assist cuff 200 to atmospheric pressure via exhaust port 208. However, during the actual blood collection cycle, valve 204 is controlled so as to alternately pressurize the circulatory assist cuff 200 (e.g., to approximately 0-60 mm of mercury) followed by depressurization.

Although not necessarily, the frequency of such periodic pressure variations in the circulatory assist cuff 200 may be is controlled to correspond to the detected pulse rate of the donor or a submultiple thereof. Each time the circulatory assist cuff 200 is pressurized, venous blood is expressed (via external pressure applied to the lower portion of the limb 26) from the donor's hand area up to the forearm into the area where phlebotomy needle 14 is located in a vein. Each time circulatory assist cuff 200 is depressurized so as to deflate, it permits the hand and forearm area to refill with arterial blood in readiness for the next inflation cycle. And, as will be appreciated by those in the art, the traditional blood pressure cuff 24 should (as is conventionally done) be maintained in a pressurized state (e.g., at appoximately 40 mmHg) throughout the blood collection cycle.

The exact configuration of the limb stimulator which interfaces with the donor's hand or arm may take many forms. For example, it may take the form of a torus which wraps around the donor's palm in the back of his hand. It might also take the form of a cuff similar to the traditional blood pressure cuff 24 sized so as to be conveniently wrappable around the donor's forearm.

Figure 3:
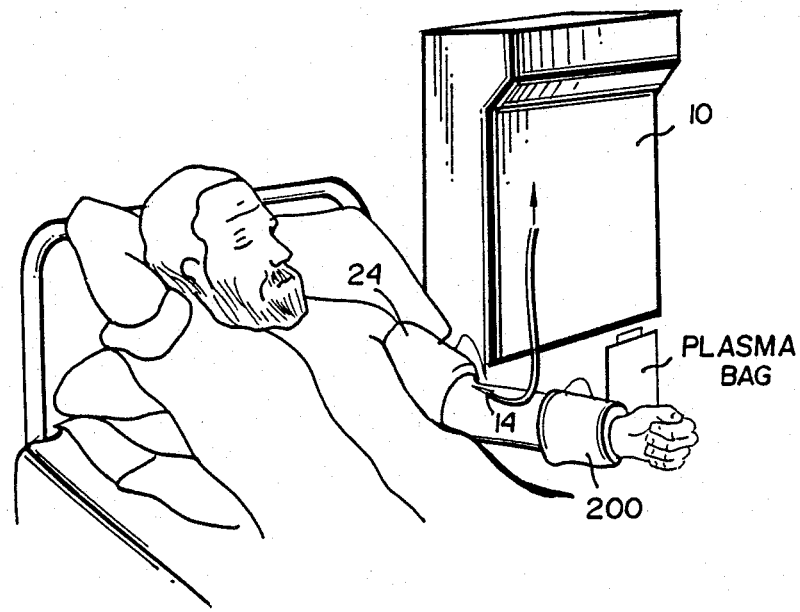
FIG. 3 is a pictorial representation of the circulatory assist cuff embodiment of this invention employed with a non-motivated or sleeping patient.

As depicted in FIG. 3, the circulatory assist cuff 200 directly compresses the donor's hand and/or part of the donor's arm at the right timing sequence so as to directly express blood upwardly within the limb towards the phlebotomy needle 14. Thus, possible confusion stemming from visual/audio/tactile stimuli is substantially avoided so that even a totally non-motivated or sleeping donor (as depicted in FIG. 3) may now be engaged in successful blood extraction procedures.

Figure 4:
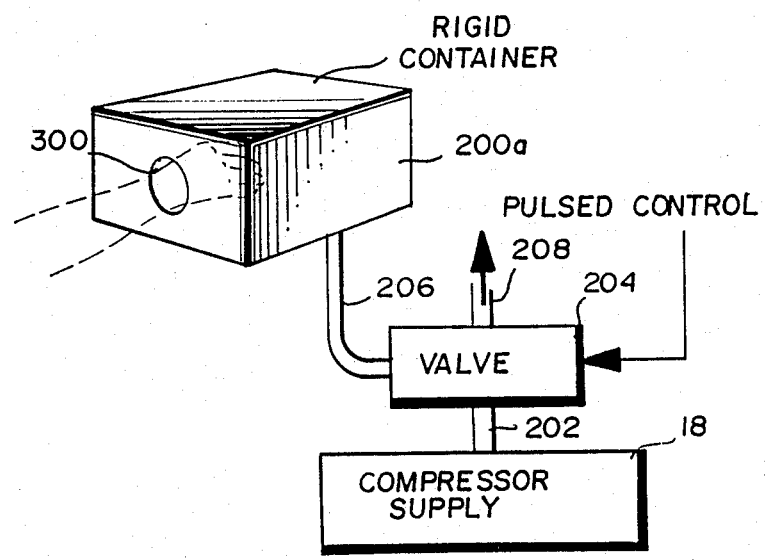
FIG. 4 illustrates an alternative embodiment of the circulatory assist cuff utilizing a pressurized rigid container sealingly engaged about the donor's hand for applying external pumping pressure thereto.

In an alternate embodiment shown at FIG. 4, the circulatory assist cuff 200 takes the form of a rigid container 200A into which the donor's hand (and perhaps a further portion of the lower limb) is sealingly inserted at 300. The pressure inside the rigid chamber 200A is then modulated at an amplitude and rate via valve 204 from the compressed air supply 18 so as to simulate conditions achieved when the donor actually flexes his fist and thus by this means apply external pumping pressures to the lower part of the limb.

Three-way valves 104 (and valve 104a, if employed) and 204 may be of conventional design as may the interconnecting tubing. Suitable output interfaces with microprocessor 12 for controlling the valves may also be of conventional design. Only relatively minor changes need be made in existing program control of the microprocessor 12 and one exemplary embodiment of such changes is depicted in the simplified flowchart of FIG. 2.

Figure 2:
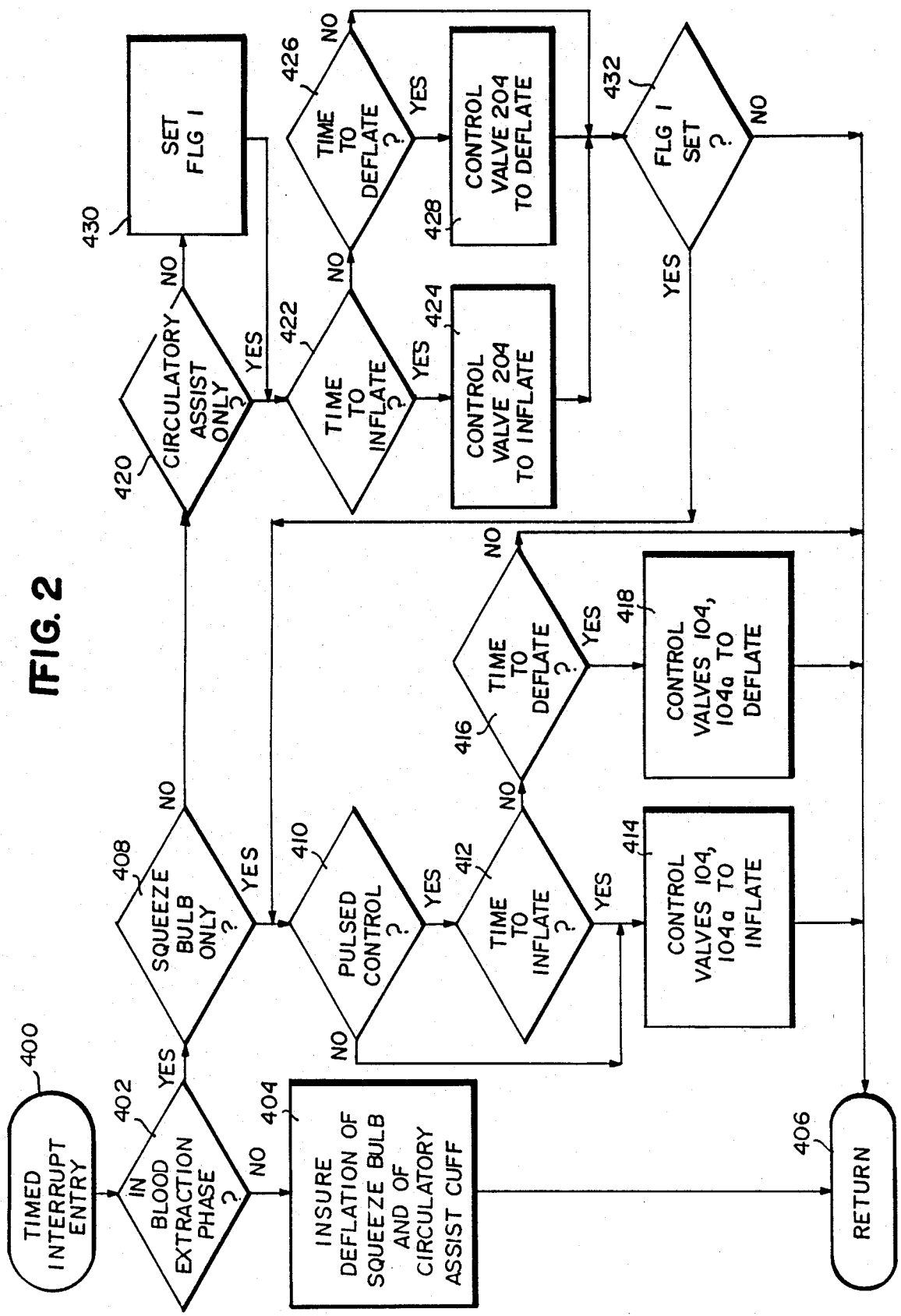
FIG. 2 is a simplified flow diagram illustrating suitable modifications which may be made in the program of the microprocessor control of FIG. 1 so as to implement this invention.

Entry at step 400 may be made once each few milliseconds where the control steps of FIG. 2 are implemented via a timed interrupt of microprocessor 12.

It will be understood that conventional controls may be used to control flow indicator 34, blood pressure cuff 24, etc. FIG. 2 is only meant to illustrate additional steps which may be added to a suitable timed interrupt software/firmware implemented routine.

A test is made at 402 to see if a blood extraction cycle is presently occurring. If not, valves 104, 104a and 204 may be reset at 404 to insure that they are deflated before a conventional return to the main control program is taken at 406.

However, if a blood extraction cycle is occurring, then control passes to 408 where a test is made (e.g., of preset switches, ROM contents, etc) to see if squeeze bulb 100 only is to be employed. If so, then another test is made at 410 to see if pulsed control of bulb 100 is to be effected. If not, valves 104, 104a are controlled at 414 to insure inflation and a return at 406 is then effected. However, if pulsed bulb operation is to be effected then tests are made of suitable timing registers at 412 and/or 416 to effect properly pulsed inflation (at block 414) or deflation (at block 418) of bulb 100 before a return at 406 is taken.

If control passes to test 420 and simultaneous use of bulb 100 and circulatory assist cuff 200 is desired, then a flag is set at 430 before control is passed to further timing register tests 422 and 426 for proper pulsed timing of inflation (424) and deflation (428) of cuff 200. A test of the flag at 432 passes control back to block 410 if the bulb 100 is also to be utilized. Otherwise, control is passed back to the main program at 406.

As will be understood, suitable timing registers may also be updated upon each entry to (or return from) the subroutine of FIG. 2 so as to permit proper decisions to be made at test points 412, 416, 422 and 426.

FIGS. 5, 5a and 5b illustrate another embodiment of the circulatory assist cuff 200. Here a series of generally parallel chambers A, B, C, D, E are provided along limb 26. These chambers are sequentially activated (as depicted in the timing diagram of FIG. 6) via an array of valves 204A-204E (powered by compressor 18—and if desired, exhausted via the compressor input) communicating with respective chambers A-E via lumen 206A-206E of the inflation/deflation tubing 206.

If desired, valves 204A-204E may be sequentially activated by expansion of the timed interrupt routine of FIG. 2 as should now be apparent to those in the art. Alternatively, a special purpose sequential or perastaltic pulse control circuit 600 may be used to sequentially inflate/deflate chambers A-E (as depicted in FIG. 6) upon receiving a trigger input signal from microprocessor 12 (e.g., as a result of a timing register test as at 422 of the FIG. 2 interrupt routine).

Pulsed control of the three-way valve 204 (and 104, 104a if desired) may be achieved in many conventional ways. For example, if pulsed operation is desired in synchronism with the donor's own pulsatile blood movements, then inputs from the pulse sensor 36 (or as conventionally sensed via cuff 24 and pressure transducer P3) may be used to control the timing registers tested at 412, 416, 422 and 426 and/or the entry to the time interrupt routine of FIG. 2. Alternatively, special purpose hard-wired and/or software controlled apparatus may be employed so as to accept pulsatile input signals (e.g., from pulse sensor 36 or from a suitable oscillator) and to provide appropriately synchronized pulsatile control inputs to the valves 204 and 104 when such pulsatile control circuits are activated via control lines output from the microprocessor 12 as a result of programmed control steps.

While only a few exemplary embodiments of this invention have been described in detail, those skilled in the art will recognize that many variations and modifications may be made in such embodiments while yet retaining many of the novel features of this invention. Accordingly, all such modifications and variations are intended to be included within the scope of the appended claims.

What is claimed is:

1. Blood extraction assist apparatus for facilitating sustained venous blood flow through a human limb towards a venous blood extraction point, said apparatus comprising:

blood processing apparatus having (a) a phlebotomy needle for fluid connection with a vein in a limb of a living body, (b) pressurizable cuff for surrounding an upper portion of said limb above a needle connection to said limb so as to substantially restrict venous blood flow while permitting arterial blood flow to continue therepast toward a lower portion of said limb where the needle connection point is located;

limb stimulus means adapted for tactile engagement with a lower portion of said limb distal to said needle connection point when activated;

control means coupled to said limb stimulus means for selectively activating said limb stimulus means for extracting and processing blood via said needle, at a time when blood flow assistance forces toward said needle connection is desired and deactivating said limb stimulus means at a time when blood flow assistance forces toward said needle connection is not desired.

2. Blood extraction assist apparatus as in claim 1 wherein said limb stimulus means includes an inflatable squeeze bulb adapted to engage a human hand and to be squeezed thereby when inflated, said control means activating said limb stimulus means by inflating said squeeze bulb to afford tactile stimulation to the human hand to flex the hand thereby assisting in venous blood movement toward the needle connection.

3. Blood extraction assist apparatus as in claim 2 wherein said limb stimulus means includes a pressurizable member substantially surrounding at least a lower portion of said limb and adapted to apply external pressure thereto, said control means activating said limb stimulus means by pressurizing said member to express venous blood through said limb toward the needle connection.

4. Blood extraction assist apparatus as in claim 1 wherein said limb stimulus means includes a pressurizable member substantially surrounding at least a lower portion of said limb and adapted to apply external pressure thereto, said control means activating said limb stimulus means by pressurizing said member to express venous blood through said limb toward the needle connection.

5. Blood extraction assist apparatus comprising
a phlebotomy needle for fluid connection with a vein in a limb of a living body;
limb stimulus means adapted for tactile engagement with a lower portion of said limb for facilitating sustained venous blood flow to said needle when activated; and
control means connected to activate said stimulus means when sustained venous blood flow is to be facilitated.

6. Blood extraction assist apparatus as in claim 5 wherein said limb stimulus means includes an inflatable squeeze bulb adapted to engage a human hand and to be squeezed thereby when inflated.

7. Blood extraction assist apparatus as in claim 5 wherein:
said limb stimulus means includes pressurizable means substantially surrounding at least a lower portion of said limb and adapted to apply external pressure thereto when pressurized so as to express venous blood through said limb to said needle; and
said control means includes means for periodically pressurizing said limb stimulus means.

8. Blood extraction assist apparatus as in claim 7 wherein said control means causes said periodic pressurizations to occur in approximate synchronism with natural pulsatile blood movements in said limb.

9. Blood extraction and processing apparatus comprising:
a phlebotomy needle for extracting venous blood from a mid-portion of a human limb;
an inflatable blood pressure cuff for engagement with an upper portion of said limb;
blood processing means connected to receive blood from said needle and to process such blood in a predetermined manner;
limb stimulating means adapted for engagement with a lower portion of said limb for selectively facilitating sustained venous blood flow to said needle when activated; and
a programmed control processor connected to control (a) inflation of said blood pressure cuff, (b) activation of said stimulating means, and (c) said blood processing means.

10. Blood extraction and processing apparatus as in claim 9 wherein said stimulating means comprises an inflatable squeeze bulb adapted to fit in a human hand and to be squeezed thereby when inflated.

11. Blood extraction and processing apparatus as in claim 9 wherein:
said stimulating means includes pressurizable means substantially surrounding at least a lower portion of said limb and adapted to apply external pressure thereto when pressurized so as to express venous blood through the limb to said needle; and
said control processor includes means for periodically pressurizing and depressurizing said stimulating means thereby periodically permitting arterial blood to pass into the lower portion of said limb and into the veins thereof whereupon it is then periodically expressed upwardly towards said needle.

12. A blood extraction assist method for facilitating sustained venous blood flow through a human limb towards a venous blood extraction point, said method comprising:
engaging a tactile stimulator with a lower portion of said limb; and
selectively activating and deactivating said tactile stimulator to facilitate an increase in the blood extraction rate.

13. A blood extraction assist method as in claim 2 wherein said tactile stimulator includes an inflatable squeeze bulb and said engaging step comprises inflating said squeeze bulb for tactile stimulation of a human hand to signal and facilitate squeezing thereof when inflated, and said activating and deactivating step includes inflating and deflating said squeeze bulb.

14. A blood extraction assistance method as in claim 13 wherein said tactile stimulator includes a pressurizable member and said engaging step includes placing said member so as to substantially surround at least a lower portion of said limb and said activating and deactivating step comprises periodically applying external pressure to said surrounded limb portion by periodically pressurizing said member so as to express venous blood through said limb toward said venous extraction point followed by depressurization of said member.

15. A blood extraction assistance method as in claim 12 wherein said tactile stimulator includes a pressurizable member and said engaging step includes placing said member so as to substantially surround at least a lower portion of said limb and said activating and deactivating step comprises periodically applying external pressure to said surrounded limb portion by periodically pressurizing said member so as to express venous blood through said limb toward said venous extraction point followed by depressurization of said member.

16. A blood extraction assistance method as in claim 12 wherein said activating and deactivating step is performed periodically during the time that sustained venous blood flow is to be facilitated.

17. Blood extraction assist method as in claim 16 wherein said periodically performed activating and deactivating step is performed in approximate synchronism with naturally occurring pulsatile blood movements in said limb.

* * * * *